(12) United States Patent
Ali et al.

(10) Patent No.: US 9,272,987 B2
(45) Date of Patent: Mar. 1, 2016

(54) DIAZENIUMDIOLATE CYCLOHEXYL DERIVATIVES

(75) Inventors: Amjad Ali, Freehold, NJ (US); Michael Man-Chu Lo, Edison, NJ (US); Lin Yan, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/115,139

(22) PCT Filed: Apr. 27, 2012

(86) PCT No.: PCT/US2012/035318
§ 371 (c)(1),
(2), (4) Date: Nov. 1, 2013

(87) PCT Pub. No.: WO2012/151114
PCT Pub. Date: Nov. 8, 2012

(65) Prior Publication Data
US 2014/0088048 A1 Mar. 27, 2014

Related U.S. Application Data

(60) Provisional application No. 61/481,367, filed on May 2, 2011.

(51) Int. Cl.
*C07C 245/24* (2006.01)
*C07C 247/06* (2006.01)
(Continued)

(52) U.S. Cl.
CPC .............. *C07C 247/06* (2013.01); *C07C 245/24* (2013.01); *C07C 291/08* (2013.01);
(Continued)

(58) Field of Classification Search
CPC ..................................................... C07C 245/24
See application file for complete search history.

(56) References Cited

U.S. PATENT DOCUMENTS

| 5,814,656 A | 9/1998 | Saavedra et al. |
| 2005/0009789 A1 | 1/2005 | Wink et al. |

(Continued)

FOREIGN PATENT DOCUMENTS

| WO | WO9746521 A1 | 5/1997 | |
| WO | WO 2009/094242 | * 7/2009 | .............. A01N 43/64 |

(Continued)

OTHER PUBLICATIONS

Saveedra et al. (Journal of Organic Chemistry (1992), 57(23), 6134-8).*

Extended European Search Report for 12779616.7, mailed Feb. 26, 2015; 6 pages.
International Preliminary Report on Patentability for PCT/US2012/035318, mailed Nov. 14, 2013; 8 pages.
(Continued)

*Primary Examiner* — Robert Havlin
(74) *Attorney, Agent, or Firm* — Nicole M. Beeler; Catherine D. Fitch

(57) ABSTRACT

A compound having the structure

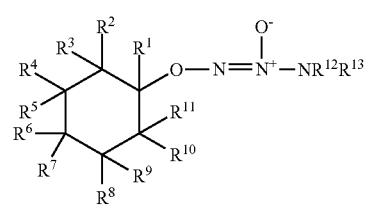

or a pharmaceutically acceptable salt thereof, wherein $R^6$ is hydrogen, —OH, —$C_{1-6}$alkyl, —O$C_{1-6}$alkyl, aryl, or halogen,
or together with $R^7$, forms an oxo group,
or together with $R^7$ and the atom to which they are attached, form a 5-7-membered carbocycle ring or a 5-7-membered heterocyclic ring having 1, 2, or 3 heteroatoms,
wherein alkyl and aryl are unsubstituted or independently mono-, di-, or tri-substituted with $R^{14}$;

$R^7$ is hydrogen, $C_{1-6}$alkyl, —$CF_3$, aryl, —O-aryl, —O—$C_{1-6}$alkyl, —C(O)O$C_{1-6}$alkyl, —C($R^{15}R^{16}$)OH, a 5-7-membered heteroaryl having 1, 2, 3 or 4 nitrogen atoms, or halogen,
or together with $R^6$, forms an oxo group,
or together with $R^6$ and the atom to which they are attached, form a 5-7-membered carbocycle ring or a 5-7-membered heterocyclic ring having 1, 2, or 3 heteroatoms
wherein alkyl, aryl and heteroaryl are unsubstituted or independently mono-, di- or tri-substituted with $R^{14}$;

$R^{12}$ is hydrogen, $C_{1-6}$alkyl, or —$(CH_2)_{1-2}$OH,
or together with $R^{13}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —$C_{1-6}$alkyl;

$R^{13}$ is —$C_{1-6}$alkyl or —$(CH_2)_{1-2}$OH,
or together with $R^{12}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —$C_{1-6}$alkyl.

15 Claims, No Drawings

(51) Int. Cl.
*C07D 231/12* (2006.01)
*C07D 249/04* (2006.01)
*C07D 317/72* (2006.01)
*C07C 291/08* (2006.01)

(52) U.S. Cl.
CPC ............ *C07D231/12* (2013.01); *C07D 249/04* (2013.01); *C07D 317/72* (2013.01); *C07B 2200/07* (2013.01); *C07C 2101/14* (2013.01)

(56) References Cited

U.S. PATENT DOCUMENTS

2005/0065194 A1 3/2005 Shankar
2005/0137191 A1 6/2005 Thatcher
2009/0186859 A1 7/2009 Velazquez et al.

FOREIGN PATENT DOCUMENTS

| WO | WO2009094242 A1 | 7/2009 |
| WO | WO2009103875 A1 | 8/2009 |
| WO | WO2010062415 A1 | 6/2010 |
| WO | WO2011043914 A1 | 4/2011 |
| WO | WO2011100384 A1 | 8/2011 |
| WO | WO2011146371 A1 | 11/2011 |
| WO | WO2012058203 A1 | 5/2012 |
| WO | WO2012122077 A1 | 9/2012 |
| WO | WO2012099770 A2 | 11/2012 |

OTHER PUBLICATIONS

Joseph E. Saavedra et al., Secondary amine/nitric oxide complex ions, R2N[N(O)NO]-. O-Functionalization chemistry, Journal of Organic Chemistry, 1992, 57, pp. 6134-6138.

\* cited by examiner

DIAZENIUMDIOLATE CYCLOHEXYL DERIVATIVES

BACKGROUND OF THE INVENTION

WO09103875 describes diazeniumdiolate dihydro indole derivatives of a specified formula for treating hypertension and cardiovascular disease. WO07144512 describes diazeniumdiolate tetrazole-biphenyl derivatives of a specified formula for treating hypertension and cardiovascular disease. US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel diazeniumdiolate cyclohexyl derivatives, useful as antihypertensive agents.

SUMMARY OF THE INVENTION

The present invention includes diazeniumdiolate cyclohexyl derivatives, including various pharmaceutically acceptable salts and hydrates of these forms, and pharmaceutical formulations comprising the diazeniumdiolate cyclohexyl derivatives.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

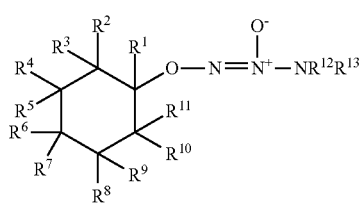

I or a pharmaceutically acceptable salt thereof, wherein
$R^1$ is hydrogen;
$R^2$, $R^3$, $R^4$, $R^5$, $R^8$, and $R^9$ are independently hydrogen or —$C_{1-6}$alkyl;
$R^6$ is hydrogen, —OH, —$C_{1-6}$alkyl, —O$C_{1-6}$alkyl, aryl, or halogen,
or together with $R^7$, forms an oxo group,
or together with $R^7$ and the atom to which they are attached, form a 5-7-membered carbocycle ring or a 5-7-membered heterocyclic ring having 1, 2, or 3 heteroatoms, wherein alkyl and aryl are unsubstituted or independently mono-, di-, or tri-substituted with $R^{14}$;
$R^7$ is hydrogen, $C_{1-6}$alkyl, —$CF_3$, aryl, —O-aryl, —O—$C_{1-6}$alkyl, —C(O)O$C_{1-6}$alkyl, —C($R^{15}R^{16}$)OH, a 5-7-membered heteroaryl having 1, 2, 3 or 4 nitrogen atoms, or halogen,
or together with $R^6$, forms an oxo group,
or together with $R^6$ and the atom to which they are attached, form a 5-7-membered carbocycle ring or a 5-7-membered heterocyclic ring having 1, 2, or 3 heteroatoms wherein alkyl, aryl and heteroaryl are unsubstituted or independently mono-, di- or tri-substituted with $R^{14}$;
$R^{10}$ and $R^{11}$ are independently hydrogen, —$C_{1-6}$alkyl, —OH, —O$C_{1-6}$alkyl, or halogen;
$R^{12}$ is hydrogen, $C_{1-6}$alkyl, or —$(CH_2)_{1-2}$OH,
or together with $R^{13}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —$C_{1-6}$alkyl;
$R^{13}$ is —$C_{1-6}$alkyl or —$(CH_2)_{1-2}$OH,
or together with $R^{12}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —$C_{1-6}$alkyl;
$R^{14}$, each time in which it occurs, is independently halogen, hydroxyl, —$C_{1-6}$alkyl, —$CF_3$, aryl or trimethylsilyl; and
$R^{15}$ and $R^{16}$ are independently hydrogen or $C_{1-6}$ alkyl;
and pharmaceutically acceptable salts thereof.

In one embodiment, the compound has the formula Ia:

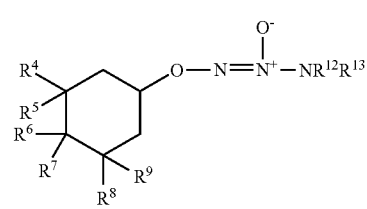

Ia

In another embodiment, $R^4$ is hydrogen or —$CH_3$.
In another embodiment, $R^5$ is hydrogen or —$CH_3$.
In another embodiment, $R^8$ is hydrogen or —$CH_3$.
In another embodiment, $R^9$ is hydrogen or —$CH_3$.
In another embodiment, $R^6$ is hydrogen, —OH, F, —$CH_3$, or —$C_6H_5$,
or together with $R^7$ forms an oxo group,
or together with $R^7$ and the atom to which they are attached, forms

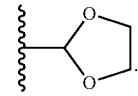

In another embodiment, $R^7$ is hydrogen, F, —$CH_3$, —$C(CH_3)_2$OH, —$CF_3$, —$C_6H_5$, —$CH_2$—$C_6H_5$, —C(O)OCH$_2$CH$_3$,

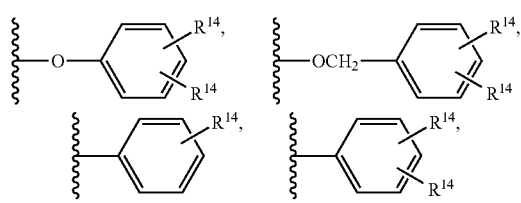

or a 5-membered heteroaryl ring having 2 or 3 nitrogen atoms, wherein $R^{14}$, each time in which it occurs, is independently halogen, —$CF_3$, aryl or trimethylsilyl,
or together with $R^6$ forms an oxo group,
or together with $R^6$ and the atom to which they are attached, forms

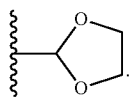

In another embodiment, $R^7$ is hydrogen, F, —$CH_3$, —$C(CH_3)_2OH$, —$CF_3$, —$C_6H_5$, —$CH_2$—$C_6H_5$, —$C(O)OCH_2CH_3$,

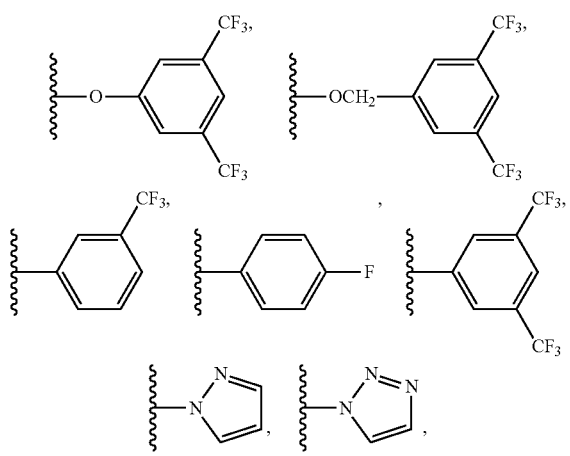

or together with $R^6$ forms an oxo group,
or together with $R^6$ and the atom to which they are attached, forms

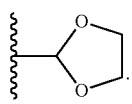

In another embodiment, $R^{12}$ is hydrogen, —$CH_3$, or —$CH_2CH_3$.
In another embodiment, $R^{13}$ is —$C(CH_3)_3$.
In another embodiment, the compound is
$O^2$-(1,4-dioxaspiro[4.5]decan-8-yl) 1-(N-tert-butyl-N-methylamino)diazen-1-ium-1,2-diolate (Ex 1)
$O^2$-(4-oxocyclohexyl) 1-(N-tert-butyl-N-methylamino)diazen-1-ium-1,2-diolate (Ex 7)
$O^2$-(4-oxocyclohexyl) 1-(N-tert-butyl-N-ethylamino)diazen-1-ium-1,2-diolate (Ex 8)
$O^2$-(4,4-difluorocyclohexyl) 1-(N-tert-butyl-N-methylamino)diazen-1-ium-1,2-diolate (Ex 9)
$O^2$-(4,4-difluorocyclohexyl) 1-(N-tert-butyl-N-ethylamino)diazen-1-ium-1,2-diolate (Ex 10)
$O^2$-(4-hydroxylcyclohexyl) 1-(N-tert-butyl-N-methylamino)diazen-1-ium-1,2-diolate (Ex 11)
$O^2$-(trans-4-hydroxylcyclohexyl) 1-(N-tert-butyl-N-methylamino)diazen-1-ium-1,2-diolate (Ex 12)
$O^2$-(cis-4-hydroxylcyclohexyl) 1-(N-tert-butyl-N-methylamino)diazen-1-ium-1,2-diolate (Ex 13)
$O^2$-{trans-4-[3,5-bis(trifluoromethyl)phenoxy]cyclohexyl} 1-(N-tert-butyl-N-methylamino)diazen-1-ium-1,2-diolate (Ex 14)
$O^2$-{cis-4-[3,5-bis(trifluoromethyl)phenoxy]cyclohexyl} 1-(N-tert-butyl-N-methylamino)diazen-1-ium-1,2-diolate (Ex 15)
$O^2$-(trans-4-{[3,5-bis(trifluoromethyl)benzyl]oxy}cyclohexyl) 1-(N-tert-butyl-N-methylamino)diazen-1-ium-1,2-diolate (Ex 16)
$O^2$-(cis-4-{[3,5-bis(trifluoromethyl)benzyl]oxy}cyclohexyl) 1-(N-tert-butyl-N-methylamino)diazen-1-ium-1,2-diolate (Ex 17)
$O^2$-(cis-4-hydroxy-4-phenylcyclohexyl) 1-(N-tert-butyl-N-methylamino)diazen-1-ium-1,2-diolate (Ex 18)
$O^2$-(trans-4-hydroxy-4-phenylcyclohexyl) 1-(N-tert-butyl-N-methylamino)diazen-1-ium-1,2-diolate (Ex 19)
$O^2$-(cis-4-phenylcyclohexyl) 1-(N-tert-butyl-N-methylamino)diazen-1-ium-1,2-diolate (Ex 32)
$O^2$-(trans-4-phenylcyclohexyl) 1-(N-tert-butyl-N-methylamino)diazen-1-ium-1,2-diolate (Ex 33)
$O^2$-{4-[3,5-bis(trifluoromethyl)phenyl]cyclohexyl} 1-(N-tert-butyl-N-methylamino)diazen-1-ium-1,2-diolate (Ex 34)
$O^2$-[trans-4-(1H-pyrazol-1-yl)cyclohexyl] 1-(N-tert-butyl-N-methylamino)diazen-1-ium-1,2-diolate (Ex 35)
$O^2$-[cis-4-(1H-pyrazol-1-yl)cyclohexyl] 1-(N-tert-butyl-N-methylamino)diazen-1-ium-1,2-diolate (Ex 36)
$O^2$-[trans-4-(1H-1,2,3-triazol-1-yl)cyclohexyl] 1-(N-tert-butyl-N-methylamino)diazen-1-ium-1,2-diolate (Ex 37)
$O^2$-[cis-4-(1H-1,2,3-triazol-1-yl)cyclohexyl] 1-(N-tert-butyl-N-methylamino)diazen-1-ium-1,2-diolate (Ex 38),
$O^2$-[trans-4-(ethoxycarbonyl)cyclohexyl] 1-(N-tert-butyl-N-ethylamino)diazen-1-ium-1,2-diolate (Ex 39),
$O^2$-[cis-4-(ethoxycarbonyl)cyclohexyl] 1-(N-tert-butyl-N-ethylamino)diazen-1-ium-1,2-diolate (Ex 40),
$O^2$-[cis-4-(2-hydroxypropan-2-yl)cyclohexyl] 1-(N-tert-butyl-N-ethylamino)diazen-1-ium-1,2-diolate (Ex 41),
$O^2$-(4,4-Dimethylcyclohexyl)-N-tert-butylamino-diazen-1-ium-1,2-diolate (Ex 42),

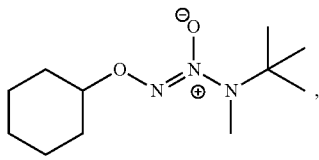

Ex 2

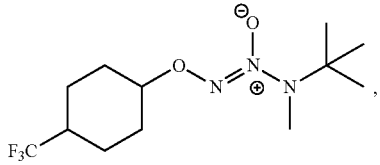

Ex 3

Ex 4
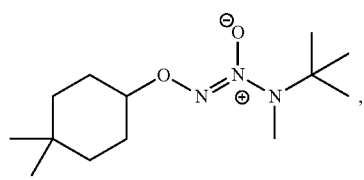

Ex 5
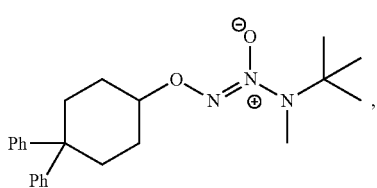

Ex 6
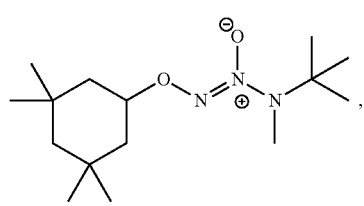

Ex 20, 21
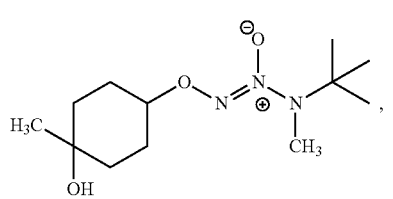

Ex 22, 23
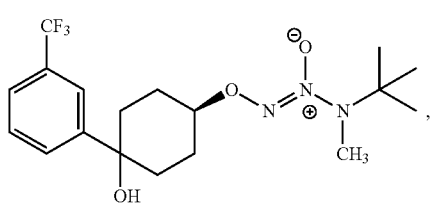

Ex 24, 25
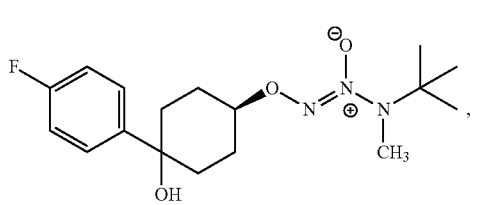

Ex 26, 27
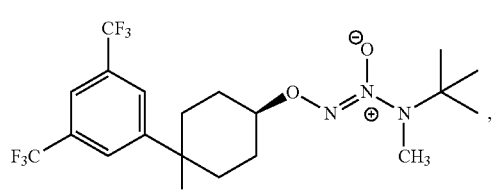

Ex 28, 29
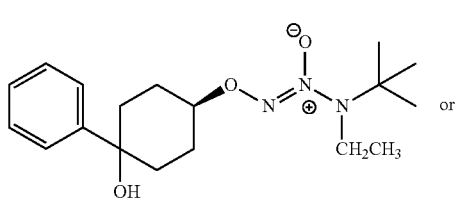

or

Ex 30, 31
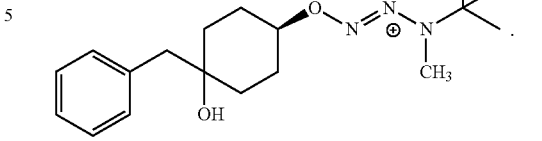

Compounds of the invention can be used to treat hypertension, treat angina, improve insulin sensitivity, and provide renal protection. The compounds can be used alone or in a fixed dose combination with other antihypertensives such as, for example, angiotensin II receptor blockers, diuretics, ACE inhibitors, β-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^{1}$H) and deuterium ($^{2}$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

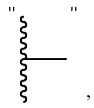

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "aryl", alone or in combination, relates to a phenyl, naphthyl or indanyl group, preferably a phenyl group. The abbreviation "Ph" represents phenyl.

The term "heteroaryl" refers to an unsaturated ring having a specified number of atom members (e.g., 5 or 6-membered), including a specified number of heteroatoms (e.g., 1, 2, 3 or 4 heteroatoms independently selected from N, O or S), e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The terms "heterocyclic" and "heterocycle" refer to a saturated ring having a specified number of atom members and a specified number of heteroatoms, in which the entire ring system (whether mono- or poly-cyclic) is saturated, e.g., a 4- to 8-membered saturated monocyclic ring or a stable 7- to 12-membered bicyclic ring system which consists of carbon atoms and one or more heteroatoms selected from N, O and S, a 5- or 6-membered heterocyclic ring having 1 or 2 heteroatoms which are N, O or S, etc. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, aryl groups may be unsubstituted, or substituted with 1 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "carbocycle" (and variations thereof such as "carbocyclic" or "carbocyclyl") as used herein, unless otherwise indicated, refers to a $C_3$ to $C_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

Except where noted herein, heteroaryl and heterocyclic rings may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0\text{-}2}$—, $HS(O)_{0\text{-}2}$—, ($C_1$-$C_6$ alkyl)$S(O)_{0\text{-}2}$($C_1$-$C_6$ alkyl)-, $HS(O)_{0\text{-}2}$($C_1$-$C_6$ alkyl)-, ($C_1$-$C_6$ alkyl)$S(O)_{0\text{-}2}$—, ($C_1$-$C_6$ alkyl)C(O)NH—, HC(O)NH—, $H_2$N—C(NH)—, —$O(C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)$C(O)_{1\text{-}2}$($C_1$-$C_6$ alkyl)-, $HC(O)_{1\text{-}2}$($C_1$-$C_6$ alkyl)-, ($C_1$-$C_6$ alkyl)$C(O)_{1\text{-}2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —$C(O)C_{1\text{-}6}$ alkyl, —$C(O)NHC_1$-$C_6$ alkyl, —$C(O)NH_2$, —$C_1$-$C_6$ alkyl$C(O)NH_2$, —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, terazosin, prazosin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compoundsincluding (i) PPAR-.gamma. agonists, such as the glitazones (e.g. troglitazone, pioglitazone, englitazone, MCC-555, rosiglitazone, balaglitazone, and the like) and other PPAR ligands, including PPAR.alpha./.gamma. dual agonists, such as KRP-297, muraglitazar, naveglitazar, Galida, tesaglitazar, TAK-559, PPAR.alpha. agonists, such as fenofibric acid derivatives (gemfibrozil, clofibrate, fenofibrate and bezafibrate), and selective PPAR.gamma. modulators (SPPAR.gamma.M's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors, glipizide, DPP-IV inhibitors such as sitagliptin, vildagliptin, alogliptin, and saxagliptin, which inhibit dipeptidyl peptidase-IV enzyme and which are useful for treating diabetes, or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 5 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, cornsweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis—General Procedures Methods of Synthesis

Several methods for preparing the compounds of this invention are described in the following Schemes and Examples. Starting materials and intermediates are made from known procedures or as otherwise illustrated. Variables are as described above unless otherwise indicated. Examples on the preparation of the sodium diazeniumdiolates can be found from the literature (Chakrapani, H.; Showalter, B. M.; Citro, M. L.; Keefer, L. K.; Saavedra, J. E. *Org. Lett.* 2007, 9, 4551-4554 and WO Patent 2009/094242).

Scheme 1 delineates a method to prepare $O^2$-alkylated diazeniumdiolates of the general structure 1-3 and 1-4 in this invention. Alcohols of the general structure 1-1 can be either commercially available or prepared from reduction of the corresponding ketone or hydroboration/oxidation of the corresponding olefin. The hydroxyl group of alcohol 1-1 can be activated for displacement at an appropriate temperature, such as room temperature, with a suitable reagent, such as methanesulfonic anhydride, trifluoromethanesulfonic anhydride, benzenesulfonyl chloride, 4-(trifluoromethyl)phenylsulfonyl chloride, in the presence or absence of a suitable base, such as N,N-diisopropylethylamine, triethylamine, N-methylmorpholine, pyridine, lutidine, or collidine, in an appropriate solvent, such as dichloromethane, dichloroethane, chloroform, acetonitrile, tetrahydrofuran, dioxane, toluene, N,N-dimethylformamide, or N-methylpyrrolidinone. The resultant sulfonate 1-2 can be displaced by an appropriate sodium diazeniumdiolate salt at an appropriate temperature, such as room temperature or elevated temperature, in an appropriate solvent, such as dichloromethane, dichloroethane, chloroform, acetonitrile, tetrahydrofuran, dioxane, dimethoxyethane, toluene, N,N-dimethylformamide, or N-methylpyrrolidinone. The stereochemistry of the resultant 1-3 at the diazeniumdiolate position is typically an inversion of that at the sulfonate carbon of 1-2 as a result of the $S_N2$ displacement. The initially formed 1-3 can be further modified to primary diaziniumdiolate 1-4 by removing $R^{S1-4}$.

Thus when $R^{S1-4}$ is an allyl group, it can be removed by treating 1-3 with a deallyation catalyst derived from Pd, Pt or Rh compounds or complexes in the presence of a reducing agent like hydrogen gas, formic acid or $NaBH_4$ in an appropriate solvent such as methanol, ethanol or isopropanol at 0-100° C.

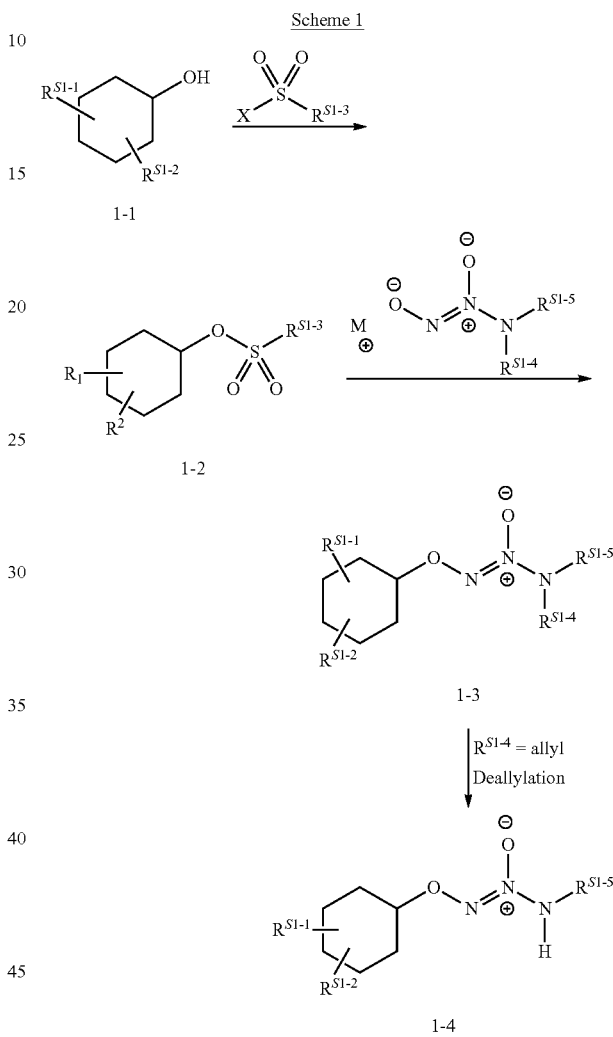

Scheme 1

$R^{S1-1}$ and $R^{S1-2}$ are independently hydrogen, halogen, substituted or unsubstituted —$C_{1-6}$alkyl or aryl, or together forms an oxo group $R^{S1-3}$ is $CH_3$, $CF_3$, Ph, or 4-$CF_3$-Ph X is Cl, $OSO_2R^{S1-3}$ where $R^{S1-3}$ is $CH_3$, $CF_3$, Ph, or 4-$CF_3$-Ph $R^{S1-4}$ and $R^{S1-5}$ are independently substituted or unsubstituted-$C_{1-6}$alkyl or —$C_{1-6}$alkenyl, or together forms an aza group M is Na, K, Cs, Ca, or Mg Scheme 2 describes a method to prepare $O^2$-alkylated diazeniumdiolates of the general structures 2-2 and 2-3 in this invention. The ketone 2-1 can be treated with a suitable organometallic reagent, such as Grignard reagents, organolithium reagents, or Ni(II)/Cr(II) reagents, in the presence or absence of an additive, such as cerium(III) chloride, at an appropriate temperature, such as room temperature, in an appropriate solvent, such as diethyl ether, tetrahydrofuran, 1,2- dimethoxyethane, or dioxane. The resultant alcohol 2-2 can be further reduced using an appropriate reducing agent, such as triethylsilane in the presence of boron trifluoride etherate or hydrogen in the presence of palladium on carbon, at an appropriate temperature such as room temperature in an appropriate solvent such as dichloromethane, dichloroethane, chloroform, acetonitrile, tetrahydrofuran, dioxane, methanol or ethanol. Racemic mixtures of 2-2 and 2-3 may be separated into their enantiomerically pure components by classical resolution methods, or by separation using chiral stationary phase HPLC chromatography.

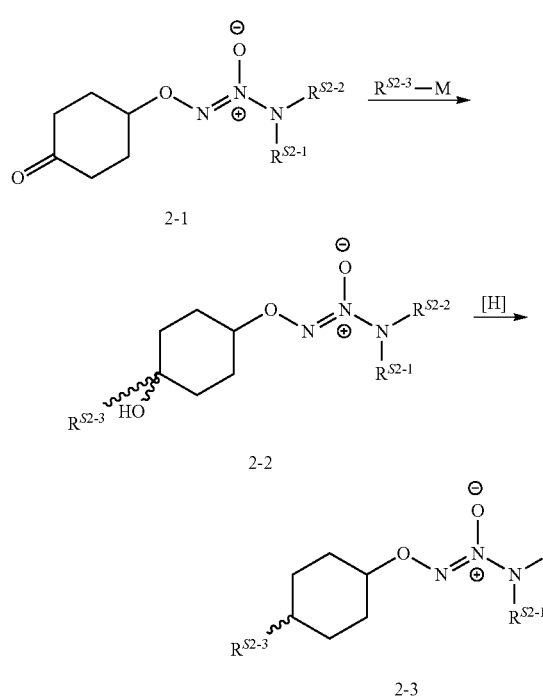

$R^{S2-1}$ and $R^{S2-2}$ are independently substituted or unsubstituted-$C_{1-6}$alkyl or —$C_{1-6}$alkenyl, or together forms an aza group.

$R^{S2-3}$ are independently substituted or unsubstituted —$C_{1-6}$alkyl or aryl.

M is MgX, where X is Cl, Br, or I.

Scheme 3 illustrates several methods to prepare $O^2$-alkylated diazeniumdiolates of the general structures 3-3 and 3-4 in this invention. The alcohol 3-1 can be activated for displacement with an suitable leaving group at an appropriate temperature, such as room temperature, with a suitable reagent, such as phosphorus tribromide, triphenylphosphine and carbon tetrabromide, methanesulfonic anhydride, trifluoromethanesulfonic anhydride, benzenesulfonyl chloride, 4-(trifluoromethyl)phenylsulfonyl chloride, in the presence or absence of a suitable base, such as N,N-diisopropylethylamine, triethylamine, N-methylmorpholine, pyridine, lutidine, or collidine, in an appropriate solvent, such as dichloromethane, dichloroethane, chloroform, acetonitrile, tetrahydrofuran, dioxane, 1,2-dimethyoxyethane, or diethyl ether. Treatment of resultant 3-2 with an appropriate amine in the presence of a suitable base, such as N,N-diisopropylethylamine, triethylamine, N-methylmorpholine, pyridine, lutidine, or collidine, at an appropriate temperature, such as room temperature, in an appropriate solvent, such as diethyl ether, tetrahydrofuran, 1,2-dimethoxyethane, dioxane, N,N-dimethylformamide, or N-methylpyrrolidinone. The alcohol 3-1 can be directly alkylated with an appropriate electrophile, such as an organic halide, in the presence of a base, such as sodium hydride, at an appropriate temperature such as room temperature in an appropriate solvent such as acetonitrile, tetrahydrofuran, dioxane, N,N-dimethylformamide, or N-methylpyrrolidinone. The alcohol 3-1 can also be alkylated under Mitsunobu conditions with an appropriate phenol at an appropriate temperature, such as room temperature, in an appropriate solvent such as dichloromethane, dichloroethane, chloroform, acetonitrile, tetrahydrofuran, or dioxane. Racemic mixtures of 3-3 and 3-4 may be separated into their enantiomerically pure components by classical resolution methods, or by separation using chiral stationary phase HPLC chromatography.

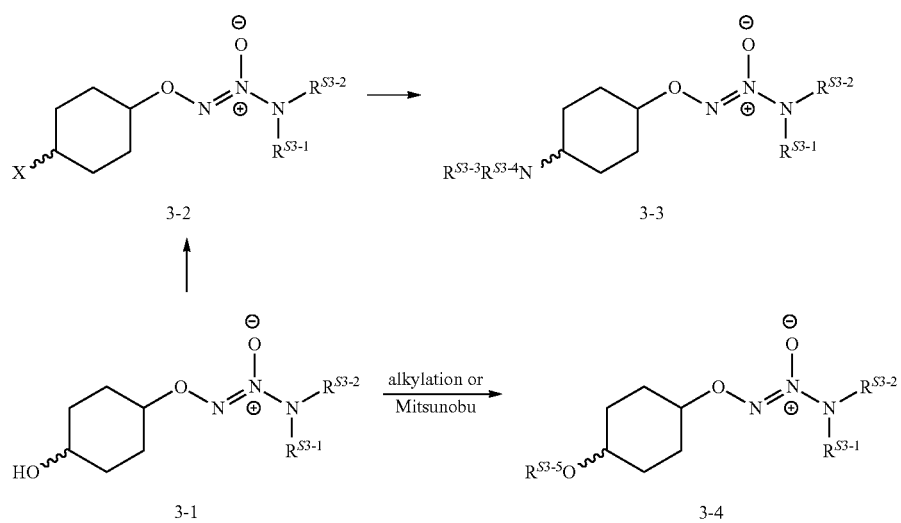

$R^{S3-1}$ and $R^{S3-2}$ are independently substituted or unsubstituted-$C_{1-6}$alkyl or —$C_{1-6}$alkenyl.

$R^{S3-3}$ and $R^{S3-4}$ are independently substituted or unsubstituted —$C_{1-6}$alkyl or —$C_{1-6}$alkenyl, or aryl, or together forms a saturated or unsaturated ring.

$R^{S3-5}$ is substituted or unsubstituted —$C_{1-6}$alkyl and aryl.

ABBREVIATIONS

Abbreviations: aqueous (aq), ethyl acetate (EtOAc), ethyl (Et); acetyl (Ac); dichloromethane (DCM), 4-(N,N-dimethylamino)pyridine (DMAP), N,N-dimethylformamide (DMF), gram(s) (g), hour(s) (h or hr), microliter(s) (μL), milligram(s) (mg), milliliter(s) (mL), millimole (mmol), mass spectrum (ms or MS), room temperature (rt), saturated aq sodium chloride solution (brine), sodium hydride (NaH), tetrabutylammonium fluoride (TBAF), trifluoroacetic acid (TFA), tetrahydrofuran (THF), and minute(s) (min).

Example 1

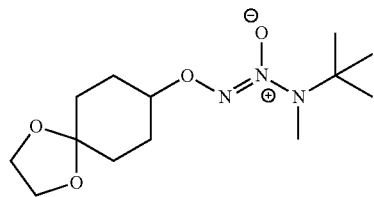 [SMILES: CN(/[N+]([O-])=N/OC1CCC2(CC1)OCCO2)C(C)(C)C]

$O^2$-(1,4-dioxaspiro[4.5]decan-8-yl) 1-(N-tert-butyl-N-methylamino)diazen-1-ium-1,2-diolate Step A: 1,4-dioxaspiro[4.5]dec-8-yl 4-(trifluoromethyl)benzenesulfonate To a solution of 1,4-dioxaspiro[4.5]decan-8-ol (82 mmol, 13.0 g) in $CH_2Cl_2$ (80 mL) at 0° C. was added 4-(trifluoromethyl)benzenesulfonyl chloride (90 mmol, 20.0 g), $Et_3N$ (123 mmol, 12.4 g) and DMAP (8.19 mmol, 1.0 g). The reaction mixture was stirred at 0° C. and then gradually warmed up to room temperature. After stirring overnight, the reaction mixture was washed with sat. $NH_4Cl$ (300 mL). The aq layer was separated and extracted with $CH_2Cl_2$ (3×300 mL). The organic layers were combined, dried over $MgSO_4$ and concentrated. Chromatography on silica gel, eluting with EtOAc and hexane, provided the title compound.

Step B: $O^2$-(1,4-dioxaspiro[4.5]decan-8-yl) 1-(N-tert-butyl-N-methylamino)diazen-1-ium-1,2-diolate A mixture of 1,4-dioxaspiro[4.5]dec-8-yl-4-(trifluoromethyl)benzenesulfonate (68.2 mmol, 25 g) and sodium (1Z)-3-tert-butyl-3-methyltriaz-1-en-1-olate 2-oxide (75 mmol, 12.7 g) in DMF (90 mL) were stirred at 45° C. overnight. After cooling down to rt, the reaction mixture was partitioned between $Et_2O$ (300 mL) and water (300 mL). The organic layer was separated, washed with brine (3×150 mL), dried over $Na_2SO_4$, and concentrated. Chromatography on silica gel, eluting with EtOAc and hexane, provided the title compound: $^1$H NMR (500 MHz, $CDCl_3$) δ 4.37 (m, 1H), 3.93 (m, 4H), 2.80 (s, 3H), 1.99 (m, 4H), 1.83 (m, 2H), 1.60 (m, 2H), 1.22 (s, 9H).

Example 2-6

The following examples were prepared using procedures analogous to those described for EXAMPLE 1 substituting appropriate alcohols for 1,4-dioxaspiro[4.5]decan-8-ol in Step A. Compounds were characterized using liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC using condition LC-1 (Waters C18 XTerra 3.5 μm 30×50 mm column with gradient 10:90-98:2 v/v $CH_3CN/H_2O$+v 0.05% TFA over 3.75 min then hold at 98:2 v/v $CH_3CN/H_2O$+v 0.05% TFA for 1.75 min; flow rate 1.0 mL/min, UV wavelength 254 nm) or LC-2 (Waters C18 XTerra 3.5 μm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm).

| EXAMPLE # | STRUCTURE | HPLC $t_R$ (min) | LCMS M + H (or M + Na) |
|---|---|---|---|
| 2 | 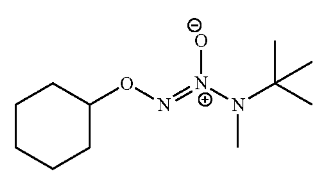 [SMILES: CN(/[N+]([O-])=N/OC1CCCCC1)C(C)(C)C] | 3.38 (LC-1) | 229.32 |
| 3 | 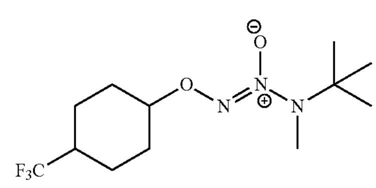 [SMILES: CN(/[N+]([O-])=N/OC1CCC(C(F)(F)F)CC1)C(C)(C)C] | 3.48 (LC-1) | 298.85 |

| EXAMPLE # | STRUCTURE | HPLC $t_R$ (min) | LCMS M + H (or M + Na) |
|---|---|---|---|
| 4 | 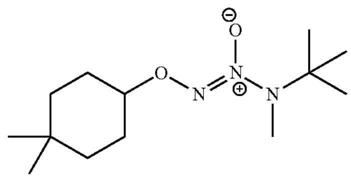 [SMILES: CN(/[N+]([O-])=N/OC1CCC(C)(C)CC1)C(C)(C)C] | 3.72 (LC-1) | 258.31 (281.28) |
| 5 | 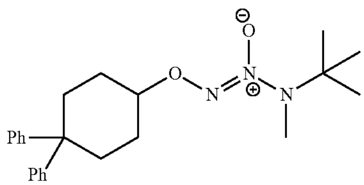 [SMILES: CN(/[N+]([O-])=N/OC1CCC(c2ccccc2)(c2ccccc2)CC1)C(C)(C)C] | 4.01 (LC-1) | 382.30 (404.27) |
| 6 | 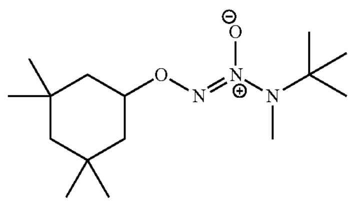 [SMILES: CN(/[N+]([O-])=N/OC1CC(C)(C)CC(C)(C)C1)C(C)(C)C] | 1.31 (LC-2) | (308.06) |

Example 7

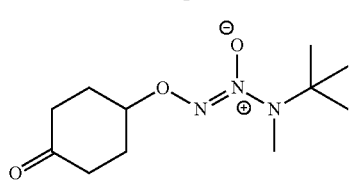 [SMILES: CN(/[N+]([O-])=N/OC1CCC(=O)CC1)C(C)(C)C]

O²-(4-oxocyclohexyl) 1-(N-tert-butyl-N-methylamino)diazen-1-ium-1,2-diolate

A solution of O²-(1,4-dioxaspiro[4.5]decan-8-yl) 1-(N-tert-butyl-N-methylamino)diazen-1-ium-1,2-diolate (EXAMPLE 1, Step B, 38.3 mmol, 11 g), formic acid (153 mmol, 70.5 g) and water (57 mmol, 1.03 g) was stirred at rt. After stirring for overnight, the reaction mixture was concentrated. Chromatography on silica gel, eluting with EtOAc and hexane, provided the title compound: ¹H NMR (500 MHz, CDCl₃) δ 4.70 (m, 1H), 2.83 (s, 3H), 2.60 (m, 2H), 2.30-2.38 (m, 4H), 2.28 (m, 2H), 1.25 (s, 9H).

Example 8

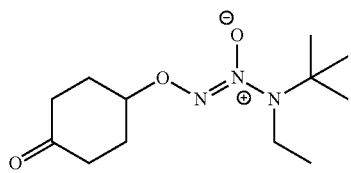 [SMILES: CCN(/[N+]([O-])=N/OC1CCC(=O)CC1)C(C)(C)C]

O²-(4-oxocyclohexyl) 1-(N-tert-butyl-N-ethylamino)diazen-1-ium-1,2-diolate

The following examples were prepared using procedures analogous to those described for EXAMPLE 7, substituting O²-(1,4-dioxaspiro[4.5]decan-8-yl) 1-(N-tert-butyl-N-ethylamino)diazen-1-ium-1,2-diolate for O²-(1,4-dioxaspiro [4.5]decan-8-yl) 1-(N-tert-butyl-N-methylamino)diazen-1-ium-1,2-diolate: ¹H NMR (500 MHz, CDCl₃) δ 4.75 (m, 1H), 3.15 (m, 2H), 2.64 (m, 2H), 2.36 (m, 4H), 2.19 (m, 2H), 1.28 (s, 9H).

Example 9

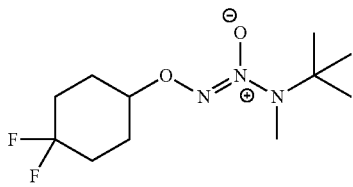 [SMILES: CN(/[N+]([O-])=N/OC1CCC(F)(F)CC1)C(C)(C)C]

O²-(4,4-difluorocyclohexyl) 1-(N-tert-butyl-N-methylamino)diazen-1-ium-1,2-diolate To a solution of Deoxofluor (4.9 mmol, 1.08 g) in toluene (20 mL) at 0° C. was added boron trifluoride diethyl etherate (0.35 mmol, 0.05 g). After stirring at 0° C. for 2 h, a solution of O²-(4-oxocyclohexyl) 1-(N-tert-butyl-N-methylamino) diazen-1-ium-1,2-diolate (EXAMPLE 7, 3.5 mmol, 0.85 g) in toluene was added. The reaction mixture was gradually warmed up to 55° C. After stirring at 55° C. for overnight, the reaction mixture was concentrated. Chromatography on silica gel, eluting with EtOAc and hexane, provided a colorless oil, which was crystallized (hexane and EtOAc) to give the title compound: ¹H NMR (500 MHz, CDCl₃) δ 4.55 (m, 1H), 2.81 (s, 3H), 1.80-2.20 (m, 8H), 1.24 (s, 9H).

Example 10

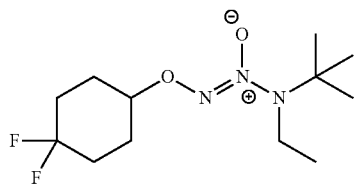 [SMILES: CCN(/[N+]([O-])=N/OC1CCC(F)(F)CC1)C(C)(C)C]

O$^2$-(4,4-difluorocyclohexyl) 1-(N-tert-butyl-N-ethylamino)diazen-1-ium-1,2-diolate The following examples were prepared using procedures analogous to those described for EXAMPLE 9 substituting O$^2$-(4-oxocyclohexyl) 1-(N-tert-butyl-N-ethylamino)diazen-1-ium-1,2-diolate for O$^2$-(4-oxocyclohexyl) 1-(N-tert-butyl-N-methylamino)diazen-1-ium-1,2-diolate: $^1$H NMR (500 MHz, CDCl$_3$) δ 4.45 (m, 1H), 3.07 (m, 2H), 1.80-2.17 (m, 8H), 1.20 (s, 9H), 1.00 (m, 3H).

Example 11

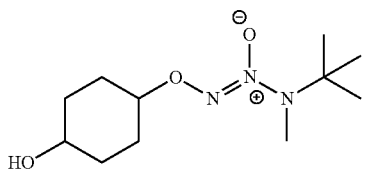 [SMILES: CN(/[N+]([O-])=N/OC1CCC(O)CC1)C(C)(C)C]

O$^2$-(4-hydroxylcyclohexyl) 1-(N-tert-butyl-N-methylamino)diazen-1-ium-1,2-diolate To a solution of O$^2$-(4-oxocyclohexyl) 1-(N-tert-butyl-N-methylamino)diazen-1-ium-1,2-diolate (EXAMPLE 7, 7 mmol, 1.7 g) in CH$_3$OH (60 mL) at 0° C. was added NaBH$_4$ (10.5 mmol, 0.40 g) in three portions. After stirring for 2 h, the reaction was quenched by addition of sat. NH$_4$Cl (100 mL) and the resulting mixture was extracted with CH$_2$Cl$_2$ (3×100 mL). The organic layers were combined, dried over MgSO$_4$ and concentrated. Chromatography on silica gel, eluting with EtOAc and hexane, provided the title compound: $^1$H NMR (500 MHz, CDCl$_3$) δ 4.30-4.37 (m, 2H), 3.73-4.10 (m, 2H), 2.80 and 2.81 (2s, 3H), 2.00-2.07 (m, 2H), 1.36-1.78 (m, 6H), 1.24 and 1.23 (2s, 9H)).

Example 12 and 13

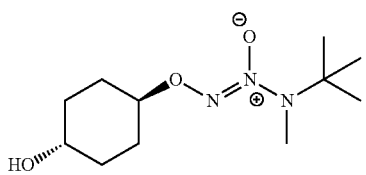

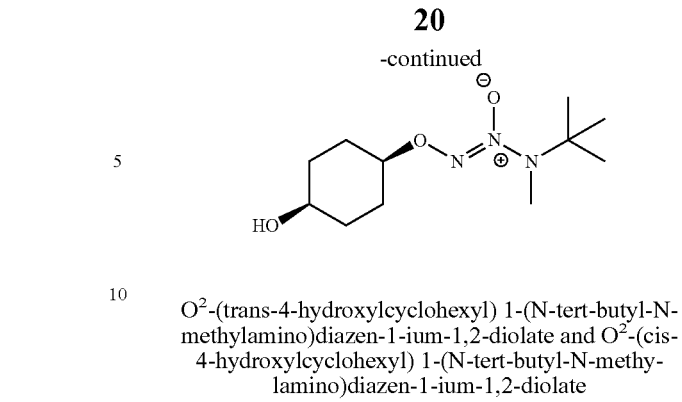

O$^2$-(trans-4-hydroxylcyclohexyl) 1-(N-tert-butyl-N-methylamino)diazen-1-ium-1,2-diolate and O$^2$-(cis-4-hydroxylcyclohexyl) 1-(N-tert-butyl-N-methylamino)diazen-1-ium-1,2-diolate The two examples were prepared from chiral separation of O$^2$-(4-hydroxylcyclohexyl) 1-(N-tert-butyl-N-methylamino)diazen-1-ium-1,2-diolate (EXAMPLE 11) using 24% isopropyl alcohol in heptane at 15 ml/min with Pirkle Covalent (R,R) Whelk-O 10/100, 25 cm×21.1 mm SER #2120401 column. The cis-isomer had a short retention time ($^1$H NMR (500 MHz, CDCl$_3$) δ 4.33 (m, 1H), 3.77 (m, 1H), 2.77 (s, 3H), 2.00-2.04 (m, 2H), 1.65-1.73 (m, 6H), 1.20 (s, 9H)) than the trans-isomer ($^1$H NMR (500 MHz, CDCl$_3$) δ 4.29 (m, 1H), 3.72 (m, 1H), 2.79 (s, 3H), 2.11 (m, 2H), 2.00 (m, 2H), 1.61-1.64 (m, 2H), 1.38-1.40 (m, 2H), 1.22 (s, 9H)).

Example 14 and 15

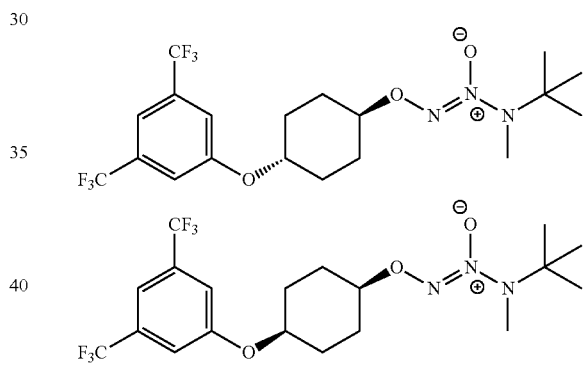

O$^2$-{trans-4-[3,5-bis(trifluoromethyl)phenoxy]cyclohexyl} 1-(N-tert-butyl-N-methylamino)diazen-1-ium-1,2-diolate and O$^2$-{cis-4-[3,5-bis(trifluoromethyl)phenoxy]cyclohexyl} 1-(N-tert-butyl-N-methylamino)diazen-1-ium-1,2-diolate To a mixture of 3,5-bis(trifluoromethyl)phenol (1.65 mmol, 400 mg), O$^2$-(4-hydroxylcyclohexyl) 1-(N-tert-butyl-N-methylamino)diazen-1-ium-1,2-diolate (EXAMPLE 11, 1.5 mmol, 368 mg), triphenylphosphine (2.25 mmol, 596 mg) in THF (40 mL) at 0° C. was added diisopropyl azodicarboxylate (2.25 mmol, 479 mg) dropwise. After 15 min, the reaction mixture was allowed to warm up to rt. After stirring over the weekend, the reaction mixture was concentrated. Chromatography on silica gel, eluting with EtOAc and hexane, provided the cis title compound: $^1$H NMR (500 MHz, CDCl$_3$) δ 7.43 (s, 1H), 7.29 (s, 2H), 4.52 (m, 1H), 4.41 (m, 1H), 2.82 (s, 3H), 2.07 (m, 2H), 1.93 (m, 2H), 1.76 (m, 2H), 1.53-1.77 (m, 2H), 1.24 (s, 9H); and the crude trans title compound, which was further purified on Chiral OJ column using isopropyl alcohol in heptane: $^1$H NMR (500 MHz, CDCl$_3$) δ 7.40 (s, 1H), 7.26 (s, 2H), 4.45 (m, 2H), 2.80 (s, 3H), 2.13 (m, 4H), 1.80 (m, 2H), 1.68 (m, 2H), 1.22 (s, 9H).

Example 16 and 17

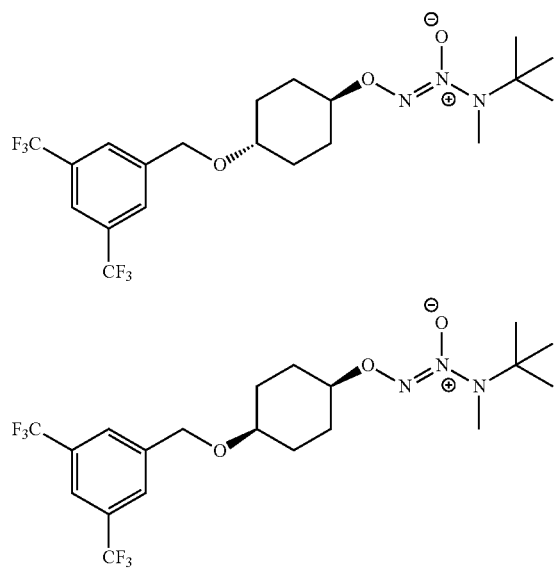 [SMILES: CN(/[N+]([O-])=N/O[C@H]1CC[C@H](OCc2cc(C(F)(F)F)cc(C(F)(F)F)c2)CC1)C(C)(C)C ; CN(/[N+]([O-])=N/O[C@H]1CC[C@@H](OCc2cc(C(F)(F)F)cc(C(F)(F)F)c2)CC1)C(C)(C)C]

O²-(trans-4-{[3,5-bis(trifluoromethyl)benzyl]
oxy}cyclohexyl) 1-(N-tert-butyl-N-methylamino)
diazen-1-ium-1,2-diolate and O²-(cis-4-{[3,5-bis
(trifluoromethyl)benzyl]oxy}cyclohexyl) 1-(N-tert-
butyl-N-methylamino)diazen-1-ium-1,2-diolate To a solution of O²-(4-hydroxylcyclohexyl) 1-(N-tert-butyl-N-methylamino)diazen-1-ium-1,2-diolate (EXAMPLE 11, 2 mmol, 491 mg) in DMF (25 mL) at 0° C. was added NaH (60% in mineral oil, 3 mmol, 120 mg). After stirring at 0° C. for half an hour, 3,5-bis(trifluoromethyl)benzyl chloride (3.0 mmol, 804 mg) was added and the resulting mixture was gradually warmed up to 40° C. After stirring overnight at 40° C., the reaction mixture was cooled down to rt, diluted with EtOAc (50 mL), and washed with brine (3×50 mL). The organic layer was separated, dried over anhydrous Na₂SO₄, and concentrated. Chromatography on silica gel, eluting with EtOAc and hexane, provided the cis title compound: ¹H NMR (500 MHz, CDCl₃) δ 7.79 (s, 3H), 4.61 (s, 2H), 4.36 (m, 1H), 3.57 (m, 1H), 2.81 (s, 3H), 2.06 (m, 2H), 1.96 (m, 2H), 1.82 (m, 2H), 1.67 (m, 2H), 1.23 (s, 9H); and the trans title compound: ¹H NMR (500 MHz, CDCl₃) δ 7.83 (s, 1H), 7.78 (s, 2H), 4.63 (s, 2H), 4.36 (m, 1H), 3.50 (m, 1H), 2.81 (s, 3H), 2.13 (m, 4H), 1.66 (m, 2H), 1.54 (m, 2H), 1.23 (s, 9H).

Example 18 and 19

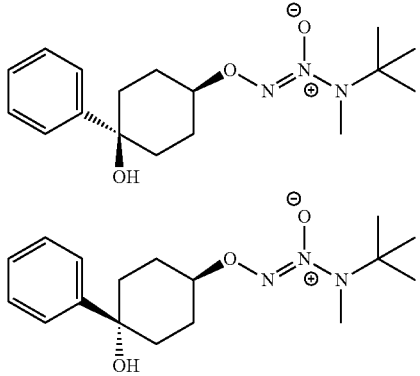

O²-(cis-4-hydroxy-4-phenylcyclohexyl) 1-(N-tert-
butyl-N-methylamino)diazen-1-ium-1,2-diolate and
O²-(trans-4-hydroxy-4-phenylcyclohexyl) 1-(N-tert-
butyl-N-methylamino)diazen-1-ium-1,2-diolate To a solution of phenyl magnesium bromide (12.33 mL 1.0 M in THF) in THF (30 mL) at 0° C. was added O²-(4-oxocyclohexyl) 1-(N-tert-butyl-N-methylamino)diazen-1-ium-1,2-diolate (EXAMPLE 7, 4.11 mmol, 1.0 g) in THF (10 mL). After stirring at 0° C. for 3 h, the reaction was quenched by adding water (50 mL). The mixture was extracted with CH₂Cl₂ (3×50 mL) and the organic layers were combined, dried over MgSO₄ and concentrated. Chromatography on silica gel, eluting with EtOAc and hexane, provided the cis title compound: ¹H NMR (500 MHz, CDCl₃) δ 7.51 (m, 2H), 7.34 (m, 2H), 7.24 (m, 1H), 4.61 (m, 1H), 2.80 (s, 3H), 2.08 (m, 4H), 1.91 (m, 4H), 1.24 (s, 9H); and the trans title compound: ¹H NMR (500 MHz, CDCl₃) δ 7.47 (m, 2H), 7.33 (m, 2H), 7.24 (m, 1H), 4.35 (m, 1H), 2.81 (s, 3H), 2.21 (m, 4H), 2.03 (m, 2H), 1.68 (m, 2H), 1.24 (s, 9H).

Example 20-31

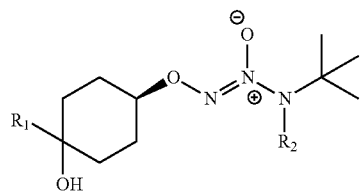

The following examples were prepared using procedures analogous to those described for EXAMPLE 18 and 19 substituting appropriate Grignard reagents for phenyl magnesium bromide.

| EXAMPLE # | Relative Stereochemistry | R⁷ | R¹² | HPLC $t_R$ (min) | LCMS M + H (or M + Na) |
|---|---|---|---|---|---|
| 20 | cis | H₃C― | CH₃ | 2.56 | (282.27) |

-continued

| EXAMPLE # | Relative Stereochemistry | R⁷ | R¹² | HPLC $t_R$ (min) | LCMS M + H (or M + Na) |
|---|---|---|---|---|---|
| 21 | trans | (CH₃)₂CH- | CH₃ | | |
| 22 | cis | 3-(F₃C)C₆H₄- | CH₃ | 3.44 | 389.41 |
| 23 | trans | 3-(F₃C)C₆H₄- | CH₃ | | |
| 24 | cis | 4-F-C₆H₄- | CH₃ | 3.24 | (362.29) |
| 25 | trans | 4-F-C₆H₄- | CH₃ | | |
| 26 | cis | 3,5-(F₃C)₂C₆H₃- | CH₃ | 3.78 | (458.2) |
| 27 | trans | 3,5-(F₃C)₂C₆H₃- | CH₃ | | |
| 28 | cis | C₆H₅- | C₂H₅ | 1.19 | (358.14) |
| 29 | trans | C₆H₅- | C₂H₅ | | |
| 30 | cis | C₆H₅CH₂- | CH₃ | 3.32 | (358.27) |

| EXAMPLE # | Relative Stereochemistry | R⁷ | R¹² | HPLC $t_R$ (min) | LCMS M + H (or M + Na) |
|---|---|---|---|---|---|
| 31 | trans | 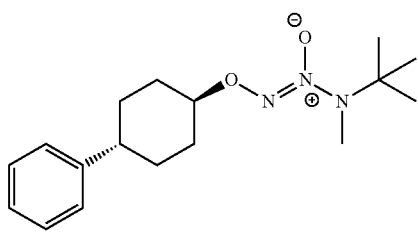 | CH₃ | | |

Example 32 and 33

O²-(cis-4-phenylcyclohexyl) 1-(N-tert-butyl-N-methylamino)diazen-1-ium-1,2-diolate and O²-(trans-4-phenylcyclohexyl) 1-(N-tert-butyl-N-methylamino)diazen-1-ium-1,2-diolate

Step A: O²-(4-phenylcyclohex-3-en-1-yl) 1-(N-tert-butyl-N-methylamino)diazen-1-ium-1,2-diolate To a solution of O²-(cis-4-hydroxy-4-phenylcyclohexyl) 1-(N-tert-butyl-N-methylamino)diazen-1-ium-1,2-diolate (Example 19, 2.18 mmol, 700 mg) was added water (3.3 mmol, 60 mg) and formic acid (87 mmol, 4.0 g). After stirring at rt overnight, the reaction mixture was concentrated. The residue was dissolved in CH₂Cl₂ (50 mL) and washed with water (30 mL). The aq layer was separated and extracted with CH₂Cl₂ (2×50 mL). The organic layers were combined, dried over Na₂SO₄ and concentrated to give the crude title compound, which was used for the next step without further purification.

Step B: O²-(cis-4-phenylcyclohexyl) 1-(N-tert-butyl-N-methylamino)diazen-1-ium-1,2-diolate and O²-(trans-4-phenylcyclohexyl) 1-(N-tert-butyl-N-methylamino)diazen-1-ium-1,2-diolate To a solution of O²-(4-phenylcyclohex-3-en-1-yl) 1-(N-tert-butyl-N-methylamino)diazen-1-ium-1,2-diolate (Step A, 1.15 mmol, 350 mg) in EtOAc (100 mL) was added Pd/C (10 wt %, 0.38 mmol, 400 mg) and the resulting mixture was stirred under atmospheric pressure of H₂ overnight at rt. The catalyst was filtered off through a pad of Celite® diatomaceous earth and washed with EtOAc. The filtrate was concentrated and the resulting residue was purified on Chiral AD column eluded with EtOH in hexane to give the cis title compound with short retention time: ¹H NMR (500 MHz, CDCl₃) δ 7.32 (m, 2H), 7.28 (m, 2H), 7.21 (m, 1H), 4.64 (m, 1H), 2.86 (s, 3H), 2.61 (m, 1H), 2.28 (m, 2H), 1.90 (m, 2H), 1.77 (m, 4H), 1.28 (s, 9H); and the trans title compound with long retention time: ¹H NMR (500 MHz, CDCl₃) δ 7.30 (m, 2H), 7.20 (m, 3H), 4.36 (m, 1H), 2.84 (s, 3H), 2.55 (m, 1H), 2.30 (m, 2H), 2.01 (m, 2H), 1.70 (m, 2H), 1.59 (m, 2H), 1.27 (s, 9H).

Example 34

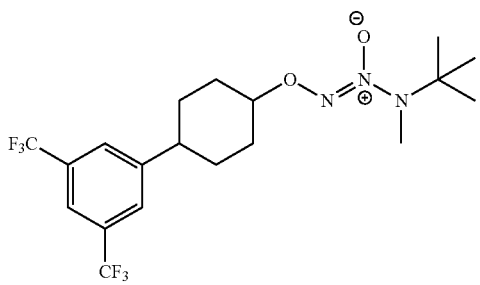 [SMILES: CN(/[N+]([O-])=N/OC1CCC(c2cc(C(F)(F)F)cc(C(F)(F)F)c2)CC1)C(C)(C)C]

O²-{4-[3,5-bis(trifluoromethyl)phenyl]cyclohexyl} 1-(N-tert-butyl-N-methylamino)diazen-1-ium-1,2-diolate The title compound was prepared using procedures analogous to procedure described for EXAMPLE 32 and 33 substituting O²-{4-[3,5-bis(trifluoromethyl)phenyl]cyclohexyl} 1-(N-tert-butyl-N-methylamino)diazen-1-ium-1,2-diolate for O²-(cis-4-hydroxy-4-phenylcyclohexyl) 1-(N-tert-butyl-N-methylamino)diazen-1-ium-1,2-diolate in Step A.

Example 35 and 36

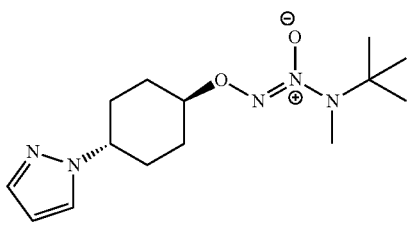

27
-continued

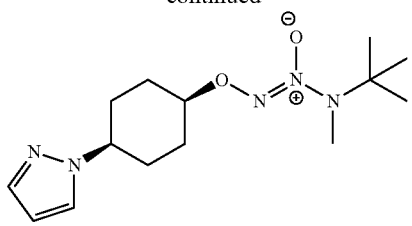

O²-[trans-4-(1H-pyrazol-1-yl)cyclohexyl] 1-(N-tert-butyl-N-methylamino)diazen-1-ium-1,2-diolate and O²-[cis-4-(1H-pyrazol-1-yl)cyclohexyl] 1-(N-tert-butyl-N-methylamino)diazen-1-ium-1,2-diolate Step A: O²-(4-{[4-(trifluoromethyl)phenyl]sulfonyl}cyclohexyl) 1-(N-tert-butyl-N-methylamino)diazen-1-ium-1,2-diolate To a solution of O²-(4-hydroxylcyclohexyl) 1-(N-tert-butyl-N-methylamino)diazen-1-ium-1,2-diolate (EXAMPLE 11, 12.23 mmol, 3.0 g) in CH₂Cl₂ (50 mL) at 0° C. was added 4-(trifluoromethyl)benzenesulfonyl chloride (13.45 mmol, 3.29 g), Et₃N (18.34 mmol, 1.86 g) and DMAP (1.223 mmol, 0.149 g). The reaction mixture was stirred at 0° C. and then gradually warmed up to rt. After stirring overnight, the reaction mixture was washed with water (100 mL). The aq layer was separated and extracted with CH₂Cl₂ (3×100 mL). The organic layers were combined, dried over MgSO₄ and concentrated. Chromatography on silica gel, eluting with EtOAc and hexane, provided the title compound.

Step B: O²-[trans-4-(1H-pyrazol-1-yl)cyclohexyl] 1-(N-tert-butyl-N-methylamino)diazen-1-ium-1,2-diolate and O²-[cis-4-(1H-pyrazol-1-yl)cyclohexyl] 1-(N-tert-butyl-N-methylamino)diazen-1-ium-1,2-diolate To a solution of O²-(4-{[4-(trifluoromethyl)phenyl]sulfonyl}cyclohexyl) 1-(N-tert-butyl-N-methylamino)diazen-1-ium-1,2-diolate (Step A, 1.54 mmol, 700 mg) in DMF (12 mL) at rt was added pyrazole (1.70 mmol, 118 mg) and cesium carbonate (3.86 mmol, 1.26 g). After stirring at rt overnight, the reaction mixture was diluted with Et₂O (70 mL) and washed with brine (3×50 mL). The organic layer was dried over MgSO₄ and concentrated. Chromatography on silica gel, eluting with EtOAc and hexane, provided the title cis compound: ¹H NMR (500 MHz, CDCl₃) δ 7.48 (d, 1H, J=2.0 Hz), 7.46 (s, 1H, J=2.0 Hz), 6.24 (t, 1H, J=2.0 Hz), 4.55 (m, 1H), 4.24 (m, 1H), 2.81 (s, 3H), 2.61 (m, 1H), 2.24 (m, 2H), 2.01-2.18 (m, 4H), 1.80 (m, 2H), 1.23 (s, 9H); and the title trans compound: ¹H NMR (500 MHz, CDCl₃) δ 7.45 (s, 1H), 7.36 (d, 1H, J=1.0 Hz), 6.24 (s, 1H), 4.31 (m, 1H), 4.11 (m, 1H), 2.76 (s, 3H), 2.27 (m, 2H), 2.25 (m, 2H), 1.89 (m, 2H), 1.69 (m, 2H), 1.19 (s, 9H).

28
Example 37

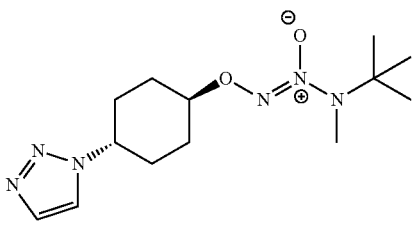 [SMILES: CN(/[N+]([O-])=N/O[C@H]1CC[C@H](n2ccnn2)CC1)C(C)(C)C]

O²-[trans-4-(1H-1,2,3-triazol-1-yl)cyclohexyl] 1-(N-tert-butyl-N-methylamino)diazen-1-ium-1,2-diolate Step A: O²-(4-azidocyclohexyl) 1-(N-tert-butyl-N-methylamino)diazen-1-ium-1,2-diolate To a solution of O²-(4-hydroxylcyclohexyl) 1-(N-tert-butyl-N-methylamino)diazen-1-ium-1,2-diolate (EXAMPLE 11, 8.15 mmol, 2.0 g) in CH₂Cl₂ (50 mL) at rt was added diisopropyl azodicarboxylate (16.31 mmol, 3.3 g), triphenylphosphine (16.31 mmol, 4.28 g) and Zn(N₃)₂/bis-pyridine complex (*Synthesis* 1990, 130) (12.23 mmol, 3.76 g). After stirring overnight, the reaction mixture was concentrated. Chromatography on silica gel, eluting with EtOAc and hexane, provided the title compound.

Step B: O²-{trans-4-[4-(trimethylsilyl)-1H-1,2,3-triazol-1-yl]cyclohexyl} 1-(N-tert-butyl-N-methylamino)diazen-1-ium-1,2-diolate and O²-{cis-4-[4-(trimethylsilyl)-1H-1,2,3-triazol-1-yl]cyclohexyl} 1-(N-tert-butyl-N-methylamino)diazen-1-ium-1,2-diolate To a solution of O²-(4-azidocyclohexyl) 1-(N-tert-butyl-N-methylamino)diazen-1-ium-1,2-diolate (Step A, 1.48 mmol, 400 mg) in toluene (3 mL) was added ethynyl(trimethyl)silane (14.44 mmol, 1.42 g). The reaction mixture was stirred at 120° C. for 2 h in a microwave reactor. The reaction mixture was concentrated. Chromatography on silica gel, eluting with EtOAc and hexane, provided the title cis compound: ¹H NMR (500 MHz, CDCl₃) δ 7.52 (s, 1H), 4.58 (m, 1H), 4.52 (m, 1H), 2.75 (s, 3H), 2.24 (m, 2H), 2.03 (m, 4H), 1.76 (m, 2H), 1.17 (s, 9H), 0.24 (s, 9H); and the title trans compound: ¹H NMR (500 MHz, CDCl₃) δ 7.48 (s, 1H), 4.47 (m, 1H), 4.33 (m, 1H), 2.76 (s, 3H), 2.29 (m, 4H), 1.90 (m, 2H), 1.73 (m, 2H), 1.18 (s, 9H), 0.25 (s, 9H).

Step C: O²-[trans-4-(1H-1,2,3-triazol-1-yl)cyclohexyl] 1-(N-tert-butyl-N-methylamino)diazen-1-ium-1,2-diolate To a solution of O²-{trans-4-[4-(trimethylsilyl)-1H-1,2,3-triazol-1-yl]cyclohexyl} 1-(N-tert-butyl-N-methylamino)diazen-1-ium-1,2-diolate (0.597 mmol, 220 mg) in THF (30 mL) was added TBAF (1M, 0.895 mL). After stirring at rt overnight, the reaction mixture was concentrated. Chromatography on silica gel, eluting with EtOAc and hexane, provided the title trans compound: ¹H NMR (500 MHz, CDCl₃)

δ 7.64 (s, 1H), 7.54 (s, 1H), 4.47 (m, 1H), 4.34 (m, 1H), 2.77 (s, 3H), 2.29 (m, 4H), 1.94 (m, 2H), 1.74 (m, 2H), 1.19 (s, 9H).

Example 38

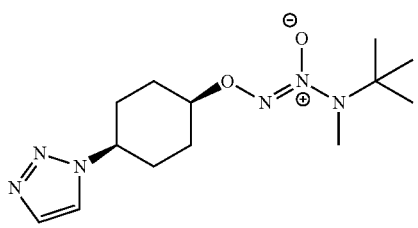 [SMILES: CN(/[N+]([O-])=N/O[C@H]1CC[C@@H](n2ccnn2)CC1)C(C)(C)C]

O$^2$-[cis-4-(1H-1,2,3-triazol-1-yl)cyclohexyl] 1-(N-tert-butyl-N-methylamino)diazen-1-ium-1,2-diolate The title compound was prepared using procedures analogous to those described for EXAMPLE 37, substituting O$^2$-{cis-4-[4-(trimethylsilyl)-1H-1,2,3-triazol-1-yl]cyclohexyl} 1-(N-tert-butyl-N-methylamino)diazen-1-ium-1,2-diolate for O$^2$-trans-4-[4-(trimethylsilyl)-1H-1,2,3-triazol-1-yl]cyclohexyl} 1-(N-tert-butyl-N-methylamino)diazen-1-ium-1,2-diolate in Step C: $^1$H NMR (500 MHz, CDCl$_3$) δ 7.69 (s, 1H), 7.61 (s, H), 4.63 (m, 2H), 2.82 (s, 3H), 2.29 (m, 2H), 2.10 (m, 4H), 1.82 (m, 2H), 1.23 (s, 9H).

Example 39

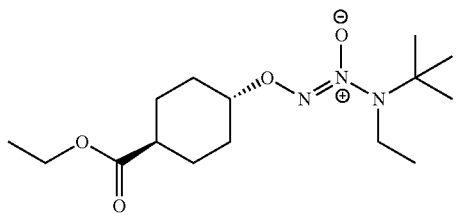 [SMILES: CCOC(=O)[C@H]1CC[C@H](O/N=[N+](\[O-])N(CC)C(C)(C)C)CC1]

O$^2$-[trans-4-(ethoxycarbonyl)cyclohexyl] 1-(N-tert-butyl-N-ethylamino)diazen-1-ium-1,2-diolate A diastereomeric mixture of the title compound was prepared using procedures analogous to those described for EXAMPLE 1, substituting ethyl 4-hydroxycyclohexane carboxylate for 1,4-dioxaspiro[4.5]decan-8-ol and sodium 1-(N-tert-butyl-N-ethylamino)diazen-1-ium-1,2-diolate for sodium 1-(N-tert-butyl-N-methylamino)diazen-1-ium-1,2-diolate. Chromatography of the diastereomeric mixture over Chiralcel OJ column, eluting with ethanol/heptane, afforded the trans diastereomer as the faster eluting peak. $^1$H NMR (500 MHz, CDCl$_3$) δ 4.41-4.48 (m, 1H), 4.13 (q, 2H, J=7.1 Hz), 3.10 (q, 2H, J=7.0 Hz), 2.37-2.43 (m, 1H), 1.93-2.04 (m, 4H), 1.68-1.77 (m, 4H), 1.24 (t, 3H, J=7.1 Hz), 1.23 (s, 9H), 1.03 (t, 3H, J=7.0 Hz).

Example 40

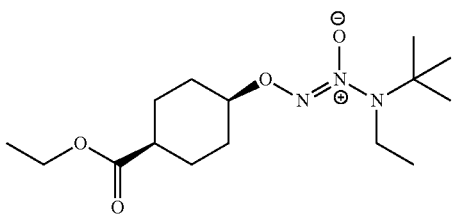 [SMILES: CCOC(=O)[C@H]1CC[C@@H](O/N=[N+](\[O-])N(CC)C(C)(C)C)CC1]

O$^2$-[cis-4-(ethoxycarbonyl)cyclohexyl] 1-(N-tert-butyl-N-ethylamino)diazen-1-ium-1,2-diolate A diastereomeric mixture of the title compound was prepared as described for EXAMPLE 39. Chromatography of the diastereomeric mixture over Chiralcel OJ column, eluting with ethanol/heptane, afforded the cis diastereomer as the slower eluting peak. $^1$H NMR (500 MHz, CDCl$_3$) δ 4.21-4.35 (m, 1H), 4.12 (q, 2H, J=7.1 Hz), 3.10 (q, 2H, J=7.0 Hz), 2.21-2.34 (m, 1H), 2.14-2.28 (m, 2H), 2.00-2.14 (m, 2H), 1.48-1.59 (m, 4H), 1.23 (t, 3H, J=7.1 Hz), 1.23 (s, 9H), 1.03 (t, 3H, J=7.0 Hz).

Example 41

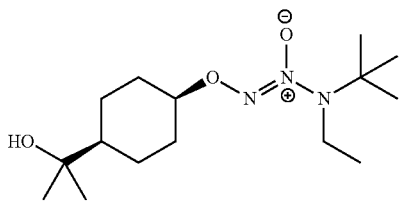 [SMILES: CCN(/[N+]([O-])=N/O[C@H]1CC[C@@H](C(C)(C)O)CC1)C(C)(C)C]

O$^2$-[cis-4-(2-hydroxypropan-2-yl)cyclohexyl] 1-(N-tert-butyl-N-ethylamino)diazen-1-ium-1,2-diolate To a tetrahydrofuran solution (20 mL) of O$^2$-[cis-4-(ethoxycarbonyl)cyclohexyl] 1-(N-tert-butyl-N-ethylamino) diazen-1-ium-1,2-diolate (EXAMPLE 40, 574 mg, 1.82 mmol) at 0° C. was slowly added methylmagnesium bromide (3.0 mL, 6.0 mmol). The reaction was allowed to warm to ambient temperature and stirred for 2 hours. The reaction was quenched with water and the organics separated. The organics were washed with brine, dried (magnesium sulfate), and concentrated in vacuo to afford the title compound. $^1$H NMR (500 MHz, CDCl$_3$) δ 4.23 (tt, 1H, J=4.5, 11.5 Hz), 3.10 (q, 2H, J=7.0 Hz), 2.19-2.27 (m, 2H), 1.89-1.98 (m, 2H), 1.51 (qd, 2H, J=3.4, 12.5 Hz), 1.27-1.35 (m, 1H), 1.23 (s, 9H), 1.18 (s, 6H), 1.12-1.20 (m, 2H), 1.03 (t, 3H, J=7.0 Hz).

Example 42

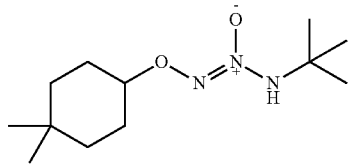

O$^2$-(4,4-Dimethylcyclohexyl)-N-tert-butylamino-diazen-1-ium-1,2-diolate

Step A: O$^2$-(4,4-Dimethylcyclohexyl)-(N-tert-butyl-N allylamino)-diazen-1-ium-1,2-diolate To a solution of 1.32 g (3.92 mmol) of 4,4-dimethylcyclohexyl-(4-trifluoromethyl)benzenesulfonate (prepared from 4,4-dimethylcyclohexanol by the method of example 1, step A) in 12 ml of DMF, 0.766 g (3.92 mmol) of sodium (N-tert-butyl-N-allylamino)-diazen-1-ium-1,2-diolate was added. The mixture was heated in a 45° C. bath for 2.5 days. The reaction was concentrated to remove most of the DMF. The residue was diluted with EtOAc and washed with water and brine. The solution was dried, concentrated. and the residue was purified on a flash column using 0-50% EtOAc-hexane to isolate the title compound. LC-MS m/e=306 (M+Na), RT=1.461 min, $^1$H NMR (500 MHz, CDCl$_3$): δ 5.8 (m, 1H), 5.3 (dd, 1H), 5.1.8 (dd, 1H), 4.24 (m, 1H), 3.65 (d, 2H), 1.2-2.0 (m, 8H), 1.28 (s, 9H), 0.95 (2s, 6H).

Step B: O$^2$-(4,4-Dimethylcyclohexyl)-N-tert-butylamino-diazen-1-ium-1,2-diolate A solution of 348 mg (1.228 mmol) of O$^2$-(4,4-dimethylcyclohexyl)-(N-tert-butyl-N allylamino)-diazen-1-ium-1,2-diolate in 3 ml of methanol and 0.13 ml formic acid was degassed and 240 mg of sulfided Pt/C (5%) was added. The mixture was heated in a 60° C. bath for 2 hr another 0.13 ml of formic acid was added. The reaction was complete after heating for another 3.5 hr. It was cooled, filtered through a pad of Celite® diatomaceous earth and the catalyst was rinsed with methanol. The filtrate was concentrated, the residue diluted with toluene and concentrated to remove formic acid. The residue was purified on a flash column using a gradient of 0-50% EtOAc-hexane to isolate the title compound. LC-MS m/e=266 (M+Na), RT=1.35 min, $^1$H NMR (500 MHz, CDCl$_3$): δ 5.74 (br s, 1H), 4.2 (m, 1H), 1.2-2.0 (m, 8H), 1.34 (s, 9H) 0.97 (2s, 6H).

ACTIVITY

Compounds of the invention were evaluated for blood pressure reduction efficacy using the following canine telemetry protocol described below.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| Example | ΔSBP (mmHg) | | | ΔPP (mmHg) | | |
|---|---|---|---|---|---|---|
| | 1-6 h | 6-12 h | 12-18 h | 1-6 h | 6-12 h | 12-18 h |
| 2 | −11 | −9 | −9 | −9 | −11 | −12 |
| 9 | −8 | −12 | −13 | −7 | −8 | −8 |
| 19 | −11 | −12 | −15 | −7 | −9 | −9 |
| 33 | −9 | −15 | −9 | −7 | −12 | −11 |

What is claimed is:
1. A compound having the formula I:

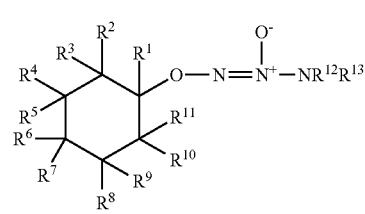

or a pharmaceutically acceptable salt thereof, wherein
R$^1$ is hydrogen;
R$^2$, R$^3$, R$^4$, R$^5$, R$^8$, and R$^9$ are independently hydrogen or —C$_{1-6}$alkyl;
R$^6$ is hydrogen, —OH, —C$_{1-6}$alkyl, —OC$_{1-6}$alkyl, aryl, or halogen,
  or together with R$^7$, forms an oxo group,
  or together with R$^7$ and the atom to which they are attached, form a 5-7-membered carbocycle ring or a 5-7-membered heterocyclic ring having 1, 2, or 3 heteroatoms,
  wherein alkyl and aryl are unsubstituted or independently mono-, di-, or tri-substituted with R$^{14}$;
R$^7$ is hydrogen, C$_{1-6}$alkyl, —CF$_3$, aryl, —O-aryl, —O—C$_{1-6}$alkyl,
  a 5-7-membered heteroaryl having 1, 2, 3 or 4 nitrogen atoms, or halogen,
  or together with R$^6$, forms an oxo group,
  or together with R$^6$ and the atom to which they are attached, form a 5-7-membered carbocycle ring or a 5-7-membered heterocyclic ring having 1, 2, or 3 heteroatoms
  wherein alkyl, aryl and heteroaryl are unsubstituted or independently mono-, di- or tri-substituted with R$^{14}$;
R$^{10}$ and R$^{11}$ are hydrogen;
R$^{12}$ is hydrogen, C$_{1-6}$alkyl, or —(CH$_2$)$_{1-2}$OH,
  or together with R$^{13}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —C$_{1-6}$alkyl;
R$^{13}$ is —C$_{1-6}$alkyl or —(CH$_2$)$_{1-2}$OH,
  or together with R$^{12}$ and the nitrogen atom to which they are attached, form a 4- to 7-membered heterocyclic ring containing one nitrogen atom and 0 or 1 oxygen atoms, wherein said ring is unsubstituted or independently mono-, di- or tri-substituted with halogen or —C$_{1-6}$alkyl;
R$^{14}$, each time in which it occurs, is independently halogen, —C$_{1-6}$alkyl, —CF$_3$, aryl or trimethylsilyl;
and pharmaceutically acceptable salts thereof.

2. A compound of claim 1, having the formula Ia:

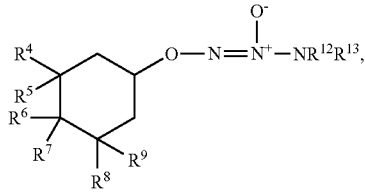

or a pharmaceutically acceptable salt thereof.

3. A compound of claim 1, wherein $R^4$ is hydrogen or —$CH_3$, or a pharmaceutically acceptable salt thereof.

4. A compound of claim 1, wherein $R^5$ is hydrogen or —$CH_3$, or a pharmaceutically acceptable salt thereof.

5. A compound of claim 1, wherein $R^8$ is hydrogen or —$CH_3$, or a pharmaceutically acceptable salt thereof.

6. A compound of claim 1, wherein $R^9$ is hydrogen or —$CH_3$, or a pharmaceutically acceptable salt thereof.

7. A compound of claim 1, wherein $R^6$ is hydrogen, —OH, F, —$CH_3$, or —$C_6H_5$, or together with $R^7$ forms an oxo group, or together with $R^7$ and the atom to which they are attached, forms

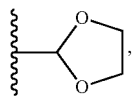

or a pharmaceutically acceptable salt thereof.

8. A compound of claim 1, wherein $R^7$ is hydrogen, F, —$CH_3$, —$CF_3$, —$C_6H_5$, —$CH_2$—$C_6H_5$,

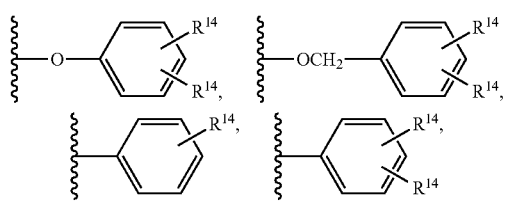

or a 5-membered heteroaryl ring having 2 or 3 nitrogen atoms, wherein $R^{14}$, each time in which it occurs, is independently halogen, —$CF_3$, aryl or trimethylsilyl, or together with $R^6$ forms an oxo group, or together with $R^6$ and the atom to which they are attached, forms

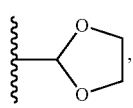

or a pharmaceutically acceptable salt thereof.

9. A compound of claim 1, wherein $R^7$ is hydrogen, F, —$CH_3$, —$CF_3$, —$C_6H_5$,

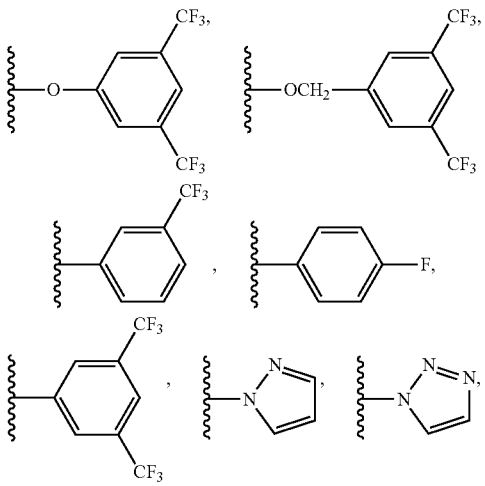

or together with $R^6$ forms an oxo group, or together with $R^6$ and the atom to which they are attached, forms

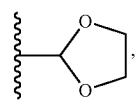

or a pharmaceutically acceptable salt thereof.

10. A compound of claim 1, wherein, $R^{12}$ is hydrogen, —$CH_3$, or —$CH_2CH_3$, or a pharmaceutically acceptable salt thereof.

11. A compound of claim 1, wherein, $R^{13}$ is —$C(CH_3)_3$, or a pharmaceutically acceptable salt thereof.

12. A compound of claim 1, which is $O^2$-(1,4-dioxaspiro[4.5]decan-8-yl) 1-(N-tert-butyl-N-methylamino)diazen-1-ium-1,2-diolate, $O^2$-(4-oxocyclohexyl) 1-(N-tert-butyl-N-methylamino)diazen-1-ium-1,2-diolate, $O^2$-(4-oxocyclohexyl) 1-(N-tert-butyl-N-ethylamino)diazen-1-ium-1,2-diolate, $O^2$-(4,4-difluorocyclohexyl) 1-(N-tert-butyl-N-methylamino)diazen-1-ium-1,2-diolate, $O^2$-(4,4-difluorocyclohexyl) 1-(N-tert-butyl-N-ethylamino)diazen-1-ium-1,2-diolate, $O^2$-(4-hydroxylcyclohexyl) 1-(N-tert-butyl-N-methylamino)diazen-1-ium-1,2-diolate, $O^2$-(trans-4-hydroxylcyclohexyl) 1-(N-tert-butyl-N-methylamino)diazen-1-ium-1,2-diolate, $O^2$-(cis-4-hydroxylcyclohexyl) 1-(N-tert-butyl-N-methylamino)diazen-1-ium-1,2-diolate, $O^2$-{trans-4-[3,5-bis(trifluoromethyl)phenoxy]cyclohexyl} 1-(N-tert-butyl-N-methylamino)diazen-1-ium-1,2-diolate, $O^2$-{cis-4-[3,5-bis(trifluoromethyl)phenoxy]cyclohexyl} 1-(N-tert-butyl-N-methylamino)diazen-1-ium-1,2-diolate, $O^2$-(trans-4-{[3,5-bis(trifluoromethyl)benzyl]oxy}cyclohexyl) 1-(N-tert-butyl-N-methylamino)diazen-1-ium-1,2-diolate, $O^2$-(cis-4-{[3,5-bis(trifluoromethyl)benzyl]oxy}cyclohexyl) 1-(N-tert-butyl-N-methylamino)diazen-1-ium-1,2-diolate, O²-(cis-4-hydroxy-4-phenylcyclohexyl) 1-(N-tert-butyl-N-methylamino)diazen-1-ium-1,2-diolate,
O²-(trans-4-hydroxy-4-phenylcyclohexyl) 1-(N-tert-butyl-N-methylamino)diazen-1-ium-1,2-diolate,
O²-(cis-4-phenylcyclohexyl) 1-(N-tert-butyl-N-methylamino)diazen-1-ium-1,2-diolate,
O²-(trans-4-phenylcyclohexyl) 1-(N-tert-butyl-N-methylamino)diazen-1-ium-1,2-diolate,
O²-{4-[3,5-bis(trifluoromethyl)phenyl]cyclohexyl} 1-(N-tert-butyl-N-methylamino)diazen-1-ium-1,2-diolate,
O²-[trans-4-(1H-pyrazol-1-yl)cyclohexyl] 1-(N-tert-butyl-N-methylamino)diazen-1-ium-1,2-diolate,
O²-[cis-4-(1H-pyrazol-1-yl)cyclohexyl] 1-(N-tert-butyl-N-methylamino)diazen-1-ium-1,2-diolate,
O²-[trans-4-(1H-1,2,3-triazol-1-yl)cyclohexyl] 1-(N-tert-butyl-N-methylamino)diazen-1-ium-1,2-diolate,
O²-[cis-4-(1H-1,2,3-triazol-1-yl)cyclohexyl] 1-(N-tert-butyl-N-methylamino)diazen-1-ium-1,2-diolate,
O²-(4,4-Dimethylcyclohexyl)-N-tert-butylamino-diazen-1-ium-1,2-diolate,

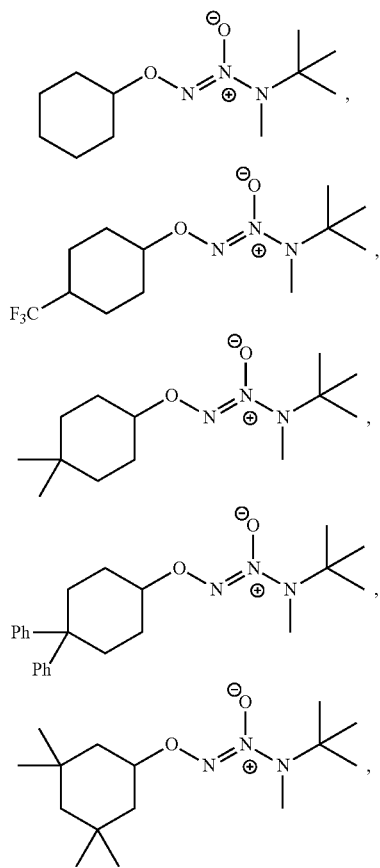

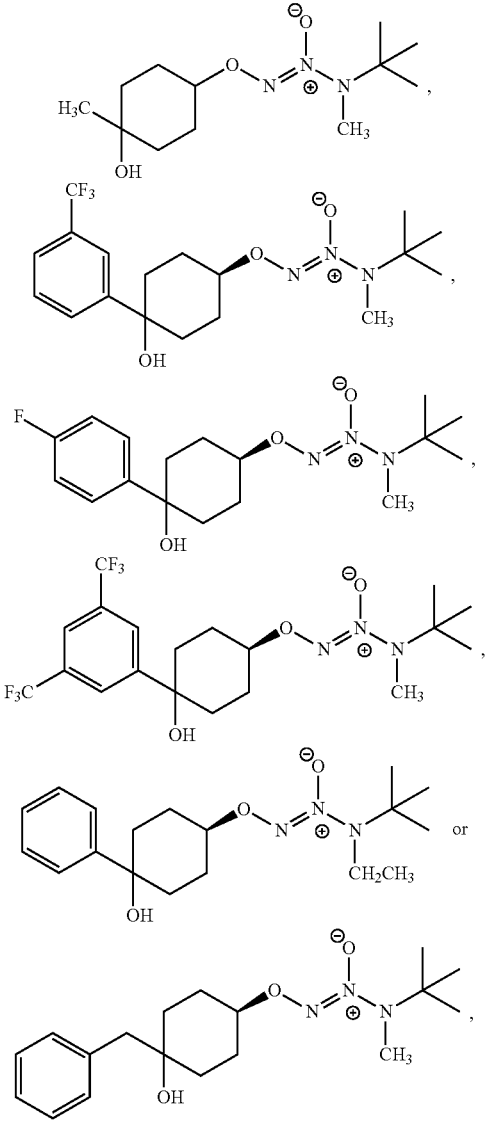

or a pharmaceutically acceptable salt thereof.

13. A pharmaceutical composition comprising a compound of claim 1, or a pharmaceutically acceptable salt thereof, and a pharmaceutically acceptable carrier.

14. A pharmaceutical composition comprising a compound of claim 12, or a pharmaceutically acceptable salt thereof, and a pharmaceutically acceptable carrier.

15. A pharmaceutical composition comprising a compound of claim 12, or a pharmaceutically acceptable salt thereof, a diuretic, and a pharmaceutically acceptable carrier.

* * * * *